(12) United States Patent
Yasue (10) Patent No.: US 9,642,516 B2
(45) Date of Patent: May 9, 2017

(54) ENDOSCOPIC SYSTEM WITH FOG PREVENTION FOR AN OBSERVATION WINDOW

(71) Applicant: OLYMPUS CORPORATION, Tokyo (JP)

(72) Inventor: Masashi Yasue, Nishitokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/954,109

(22) Filed: Nov. 30, 2015

(65) Prior Publication Data

US 2016/0081541 A1    Mar. 24, 2016

Related U.S. Application Data

(63) Continuation of application No. PCT/JP2014/077164, filed on Oct. 10, 2014.

(30) Foreign Application Priority Data

Oct. 11, 2013    (JP) .................................. 2013-214128

(51) Int. Cl.
*A61B 1/04* (2006.01)
*A61B 1/12* (2006.01)
(Continued)

(52) U.S. Cl.
CPC .......... *A61B 1/127* (2013.01); *A61B 1/00009* (2013.01); *A61B 1/00027* (2013.01);
(Continued)

(58) Field of Classification Search
CPC ......... A61B 1/126; A61B 1/127; A61B 1/128; A61B 1/00009; G02B 23/2476; G02B 27/0006; H04N 2005/2255
See application file for complete search history.

(56) References Cited

U.S. PATENT DOCUMENTS

2006/0069306 A1*  3/2006  Banik ................ A61B 1/00068
                                                      600/118
2007/0073108 A1*  3/2007  Takahashi .............. A61B 1/051
                                                      600/169

(Continued)

FOREIGN PATENT DOCUMENTS

CN    102762160 A     10/2012
JP    H11-318810 A    11/1999
(Continued)

OTHER PUBLICATIONS

English translation of International Preliminary Report on Patentability dated Apr. 21, 2016, together with the Written opinion received in related International Application No. PCT/JP2014/077164.

(Continued)

*Primary Examiner* — John P Leubecker
(74) *Attorney, Agent, or Firm* — Scully, Scott, Murphy & Presser, P.C.

(57) ABSTRACT

An endoscopic system uses the distribution of a luminance level of a photographic image taken by an imaging unit at the distal end of an endoscope to determine whether an observation window has fogged up, and then raises the temperature by a heater and remove the fog on the observation window.

4 Claims, 5 Drawing Sheets

(51) Int. Cl.
*G02B 23/24* (2006.01)
*G02B 27/00* (2006.01)
*A61B 1/00* (2006.01)
*H04N 5/225* (2006.01)

(52) U.S. Cl.
CPC ............ *A61B 1/00057* (2013.01); *A61B 1/04* (2013.01); *A61B 1/128* (2013.01); *G02B 23/2476* (2013.01); *G02B 27/0006* (2013.01); *H04N 2005/2255* (2013.01)

(56) References Cited

U.S. PATENT DOCUMENTS

| | | | | |
|---|---|---|---|---|
| 2010/0168624 | A1* | 7/2010 | Sliwa | A61B 6/12 601/3 |
| 2010/0268027 | A1* | 10/2010 | Aono | A61B 1/0008 600/109 |
| 2011/0245608 | A1* | 10/2011 | Takahashi | A61B 1/00096 600/109 |
| 2012/0116222 | A1* | 5/2012 | Sawada | A61B 17/3206 600/439 |
| 2012/0182409 | A1* | 7/2012 | Moriyama | A61B 1/00006 348/65 |
| 2013/0310644 | A1* | 11/2013 | Ichimura | A61B 1/127 600/109 |
| 2014/0272765 | A1* | 9/2014 | Andreiko | A61B 1/00006 433/27 |

FOREIGN PATENT DOCUMENTS

| | | |
|---|---|---|
| JP | 2015-512827 A | 1/2006 |
| WO | WO 2010/047396 A1 | 4/2010 |
| WO | WO 2012/035923 A1 | 3/2012 |

OTHER PUBLICATIONS

International Search Report dated Nov. 11, 2014 issued in PCT/JP2014/077164.
Japanese Office Action dated Apr. 21, 2015 issued in JP 2015-512827.
Chinese Office Action dated Jan. 22, 2017 in related Chinese Patent Application No. 201480040397.5.

* cited by examiner

ENDOSCOPIC SYSTEM WITH FOG PREVENTION FOR AN OBSERVATION WINDOW

CROSS-REFERENCE TO RELATED APPLICATIONS

This is a Continuation Application of PCT Application No. PCT/JP2014/077164, filed Oct. 10, 2014, which was published under PCT Article 21(2) in Japanese.

This application is based upon and claims the benefit of priority from Japanese Patent Application No. 2013-214128, filed Oct. 11, 2013, the entire contents of which are incorporated herein by reference.

BACKGROUND OF THE INVENTION

1. Field of the Invention

The present invention relates to an endoscopic system having a fog prevention function of an observation window in an insertion portion of an endoscope.

2. Description of the Related Art

In general, an observation window disposed at the distal end of an insertion portion of an endoscope is at a temperature equal to an outside ambient temperature of, for example, approximately 25° C. before being inserted into a lumen that is an observation target. The environment inside the lumen is at a temperature of approximately 37° C. and at a humidity of nearly 100%. Thus, if moisture in the lumen adheres to the surface of a lens and generates fog or waterdrops thereupon due to a temperature difference between the temperature of the lens of the observation window and the temperature inside the lumen at the time of insertion, an observation image becomes difficult to view. For example, a configuration known as a technique for removing the fog injects a cleaning fluid from an injection hole disposed in the vicinity of the observation window to remove the fog. However, the observation window again fogs up if its temperature is low.

Thus, for example, Jpn. Pat. Appln. KOKAI Publication No. 2006-282 suggests a configuration in which a heater serving as a heat source is disposed in the vicinity of an objective optical system serving as an observation window to prevent or remove the fog on the observation window. In Patent Literature 1, a temperature sensor for controlling the temperature of the heater is disposed in the distal end of an insertion portion in the vicinity of the heater, in addition to an electric power supply wire laid for supplying electricity to the heater, and a communication wire laid for acquiring temperature information.

As disclosed in Jpn. Pat. Appln. KOKAI Publication No. 2006-282 described above, feedback control that uses the temperature sensor is normally performed for the temperature control of the heater. Therefore, if the observation window fogs up when inserted in the lumen, the heater is heated on the basis of the temperature detected by the temperature sensor so that the fog on the observation window can be removed. When there is a large temperature difference between the temperature of the lens of the observation window and the temperature inside the lumen, the heater is heated in advance for temperature adjustment to raise the temperature of the observation window before insertion so that the temperature may be substantially the same as the temperature of an observation target.

BRIEF SUMMARY OF THE INVENTION

According to an embodiment of the present invention, there is provided an endoscopic system comprising: an endoscope in which an observation window is disposed at a distal end and which has an insertion portion to be inserted into a lumen; an imaging unit having an imaging surface comprising pixels to convert, into an image signal, an observation image which is focused through the observation window; a fog prevention heater disposed in the vicinity of the observation window; a luminance level detection section which detects the distribution of a luminance level resulting from the image signal output by the pixels of the imaging unit; a determination section which compares the distribution of the luminance level with a preset first determination standard and further compares the distribution of the luminance level with a threshold that is a preset second determination standard, and makes a determination so that the fog prevention heater performs a temperature raising operation on the basis of the comparisons; and a heater power supply which drives the fog prevention heater to raise the temperature of the observation window in accordance with the determination result in the determination section.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE PREFERRED EMBODIMENT

Hereinafter, an embodiment of the present invention is described in detail with reference to the drawings.

Figure 1:
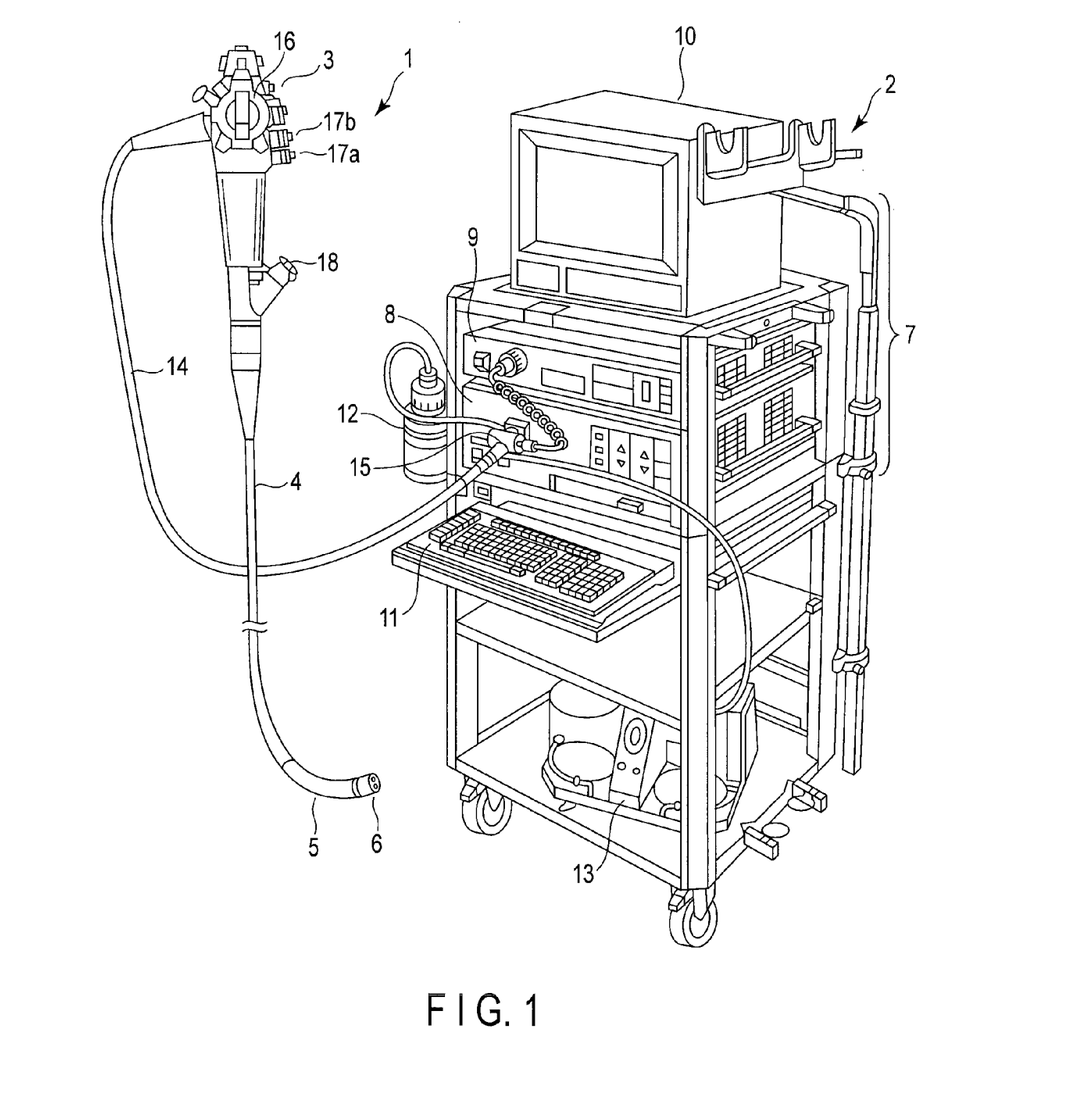
FIG. 1 is a diagram showing an overall configuration example of an endoscopic apparatus having an imaging unit in an endoscopic body as a medical instrument of the present invention.

FIG. 1 is a diagram showing an overall configuration example of an endoscopic system having a fog prevention configuration in the distal end of an insertion portion as a medical instrument of the present invention.

An endoscopic apparatus according to the present embodiment generally comprises an endoscopic body 1, and an endoscopic instrument 7 serving as various external devices mounted on a movable trolley 2. Although a flexible scope is described below by way of example, a rigid scope can also be mounted.

The endoscopic body 1 comprises an insertion portion (flexible tube) 4 which is inserted into a body cavity that is an observation target, a bending portion 5, and a later-described distal end 6 provided on the distal side of the insertion portion 4, and an endoscopic operation portion 3 which is provided on the proximal side and which is operated to bend the bending portion 5. In the following explanation, the side of the bending portion 5 is referred to as the distal side, and the side of the operation portion 3 is referred to as the proximal side.

The endoscopic instrument 7 has a light source device 8 which generates illumination light to be applied to an observation target part, a video processor 9 which subjects a captured video signal to predetermined image processing, a monitor 10 which displays the video signal as an observation image, and a keyboard 11 or the like which is an input section.

Furthermore, a bottle 12 which retains a fluid used for cleaning, etc. (cleaning fluid: a fluid mainly containing water such as a physiological saline solution, etc.) is removably attached to the trolley 2. The endoscopic instrument 7 includes an air supply pump unit (not shown). Moreover, a suction unit 13 which sucks a fluid or gas injected from a later-described cleaning nozzle in the body cavity and mucus is stored on a shelf of the trolley 2.

The endoscopic body 1 and the light source device 8 are connected to each other by a connector 15 via a universal cable 14. The universal cable 14 not only includes a light guide comprising optical fibers, but also includes signal wires which transmit video signals, and a supply path (gas/fluid supply channel) and a discharge path comprising tubes for the gas and fluid. The connector 15 connected to the universal cable 14 on the side of the endoscopic instrument 7 branches into a signal line, a tube, and a light guide which are respectively connected to the video processor 9, the suction unit 13, and the light source device 8. The endoscopic operation portion 3 is provided with a bending operation portion 16 for bending the bending portion 5, for example, in vertical and horizontal directions which intersect at right angles with each other relative to the insertion direction, a gas/fluid supply button 17a, and a suction operation button 17b. An insertion opening 18 of a forceps channel which passes through the insertion portion 4 from a channel opening disposed at the distal end is provided on the proximal side of the insertion portion 4 between the insertion portion 4 and the endoscopic operation portion 3.

The distal end 6 of the endoscopic body 1 is formed into a circular cylindrical shape by a rigid material, and is provided, in the distal end face, with an illumination window to apply at least illumination light, and an observation window 21 to observe the observation target part. Although not shown, a nozzle for injecting the fluid is disposed in the vicinity of the observation window on the distal end face. The observation window is configured by an optical lens, and applies to the observation target part the illumination light which has been guided from the light source device 8 through the optical fiber.

Figure 2:
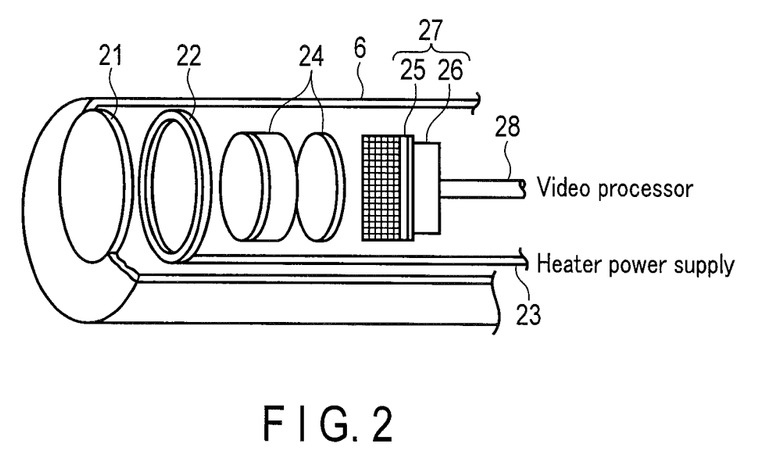
FIG. 2 is a sectional view showing the internal structure of the distal end of the endoscopic body.

As shown in FIG. 2, arranged in the distal end 6 is the observation window (cover glass) 21 comprising an objective lens in the distal end face, and arranged along the optical axis direction of the observation window 21 is an annular-shaped fog prevention heater 22, an imaging optical system 24 comprising lens groups, an image pickup device 25, and an image processing section 26. The image pickup device 25 photoelectrically converts an observation optical image formed on an imaging surface to generate a video signal. It is possible to use, as the image pickup device 25, for example, a CCD or a CMOS image sensor in which multiple image pickup devices are arranged in a plane (in matrix form) so that at least addresses can be identified. The image pickup device 25 is disposed integrally with the image processing section 26, and constitutes an imaging unit 27.

The fog prevention heater 22 is annular-shaped to ensure the optical path of the observation window 21, is located close to the circumferential portion of the observation window 21, or is in abutment with the circumferential portion of the observation window 21 via a heat conducting member, and is disposed to raise the temperature toward the center of the lens from the lens circumferential side. The fog prevention heater 22 is made of a highly resistant material, and generates heat due to electrical conduction. When the distal end 6 is made of a metallic material, the fog prevention heater 22 is electrically insulated with an insulating member intervening between the fog prevention heater 22 and the inner surface of the distal end 6. In the following explanation, a fog prevention operation suggests an operation of preventing or removing the fog on the observation window.

In such a configuration, the observation image which has passed through the observation window 21 is focused by the imaging optical system 24 on the imaging surface of the image pickup device 25 disposed in the rear on the optical axis, photoelectrically converted into an electric signal, and generated as an imaging signal by the image processing section 26. This imaging signal is sent to the video processor 9 through a video signal wiring line 28 (and the universal cable 14). The video processor 9 subjects the imaging signal to predetermined image processing, and outputs the signal to the monitor 10.

Figure 3:
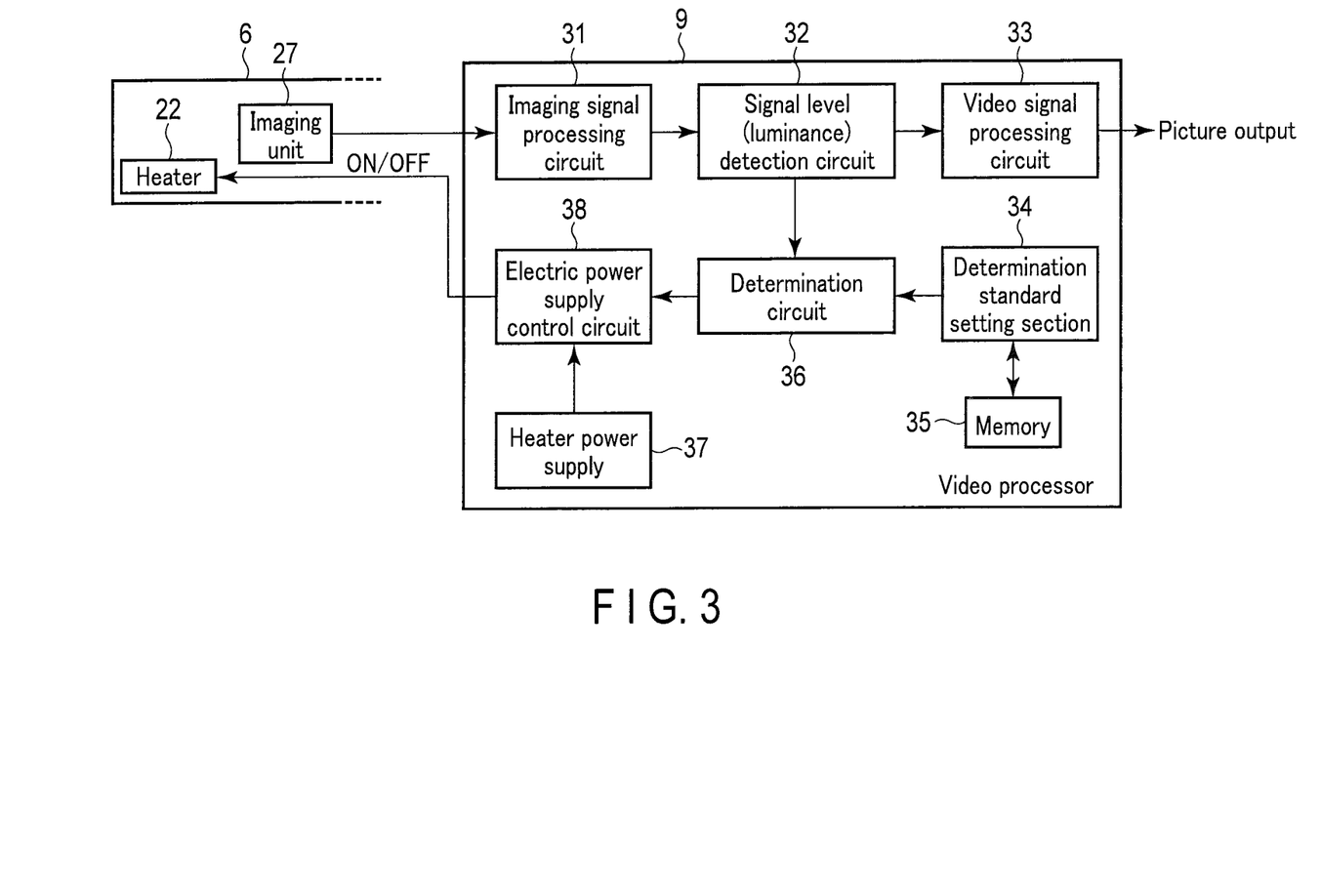
FIG. 3 is a block diagram showing the configuration of a video processor.

FIG. 3 is a diagram showing the block configuration for controlling the fog prevention operation for the objective lens in the distal end 6. In FIG. 3, components for performing the fog prevention operation in the present embodiment are selectively shown, and components which are not shown but which are provided in a general video processor are considered to be installed.

The video processor 9 according to the present embodiment comprises an image processing section 31 which removes noise from the imaging signal and performs amplification, a luminance level detection circuit 32 which detects a distribution obtained by the luminance level of the imaging signal, a video signal processing circuit 33 which generates a video signal for monitor display, a determination standard setting unit 34 which sets a determination standard, a memory 35 which stores determination standards, a determination circuit 36 which determines whether to turn on or off the fog prevention heater 22 based on the determination standard, a heater power supply 37 which outputs electric power to be supplied to the fog prevention heater 22, and an electric power supply circuit 38 which supplies electric power to the fog prevention heater 22 in accordance with the determination result.

The fog prevention operation for the observation window according to the present embodiment is described.

Figure 4:
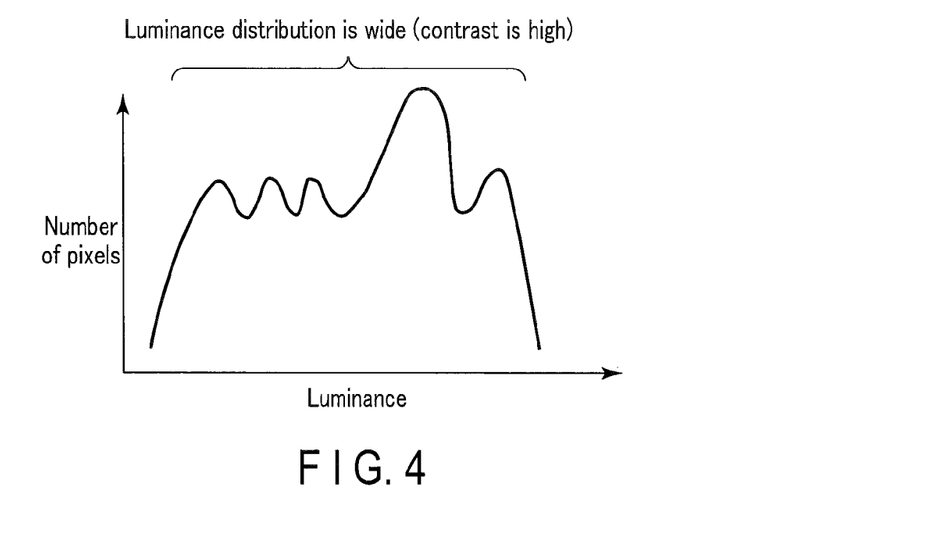
FIG. 4 is a graph showing an example of the distribution of a luminance level in the case where an observation window has not fogged up.

Normally, the contrast level (luminance distribution) of an obtained video signal is changed by whether or not the surface of the observation window 21 has fogged up. For example, in the example of a feature shown in FIG. 4, the luminance distribution of a video signal is wide (the contrast is high) in the case where the observation window 21 has not fogged up, and a proper observation image has entered the image pickup device 25. In the example of a feature shown in FIG. 5, the luminance distribution of a video signal is narrow (the overall contrast is low) in the case where the observation window 21 has fogged up, and a dimmed observation image has entered the image capture device 25.

In the configuration according to the present embodiment, the image processing section 31 has a filter circuit, an amplification circuit, and others, and the image processing section 31 performs noise reduction and amplification processing for the imaging signal received from the imaging unit 27 disposed at the distal end. The luminance level detection circuit 32 detects a distribution obtained by the luminance level of the imaging signal shown in FIG. 5, which will be described later. The video signal processing circuit 33 processes the imaging signal output from the image processing section 31 into a video signal to be displayed on the monitor 10. The memory 35 stores the determination standards, which will be described later, as a table or parameters. It should be understood that the memory 35 may be used as a single memory, or a memory attached to a control section (e.g. a personal computer) for controlling an endoscopic system may be used.

The determination standard setting unit 34 sets a determination standard selected by a selection switch (not shown in the drawings). The determination standard is set, for example, by selecting a later-described observation field displayed on the monitor 10. The determination circuit 36 compares the detected distribution of the luminance level (or referred to as a luminance distribution) with the set determination standard serving as a threshold, and thereby determines whether or not to raise the temperature of the fog prevention heater 22. This determination continues during the observation operation, and detection and determination by comparison are successively performed at predetermined time intervals.

Figure 5:
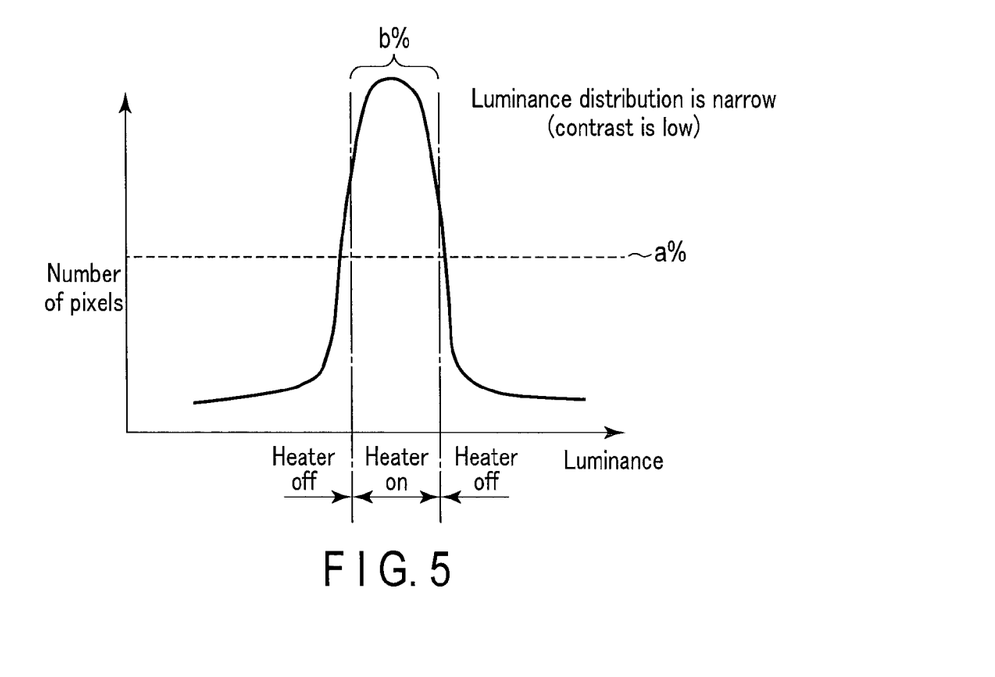
FIG. 5 is a graph showing an example of the distribution of a luminance level in the case where the observation window has fogged up.

In this determination, the observation window 21 is determined to have fogged up below the value of the width (luminance range b: b % shown in FIG. 5) of the distribution centering at the peak value of the distribution of the luminance level in the comparison, or above a preset threshold (a % shown in FIG. 5). These determinations may be made by one of the width of the distribution or the threshold, or may use both the width of the distribution and the threshold as the determination standards. The set values of a and b set in the determination standard setting unit 34 are numerical values that vary depending on the design and structure of the insertion portion, and a weight can be set for each of the later-described observation fields. Empirically, the set value can be set to a height of about 50% of the overall luminance. The set value of b can be set to, for example, a width of about 50% to 70%. The peak of the luminance level shown in FIG. 5 is not exclusively the central position of the detected luminance range.

The electric power supply circuit 38 supplies electric power to the fog prevention heater 22 from the heater power supply 37 in accordance with the determination result in the determination circuit 36, and raises the temperature of the observation window 21 to about 40° C. or less to remove the fog. If the fog on the observation window 21 is removed, the distribution of the luminance level changes to the characteristic shown in FIG. 4, and the distributed luminance level becomes higher.

In general, the observation with an endoscope varies according to an observation target depending on whether to watch the screen central side or screen peripheral side in a display screen appearing on the monitor 10. In the present embodiment, a fog position (luminance change position) is weighted by the position on the display screen (imaging surface) to be watched, that is, the position (address) of a pixel. The weighting in the present embodiment is classified by the fields (parts) of the observation target as below.

[Selection 1] Flexible Scope (Lung, Esophagus, Duodenum) Field

Figure 6A:
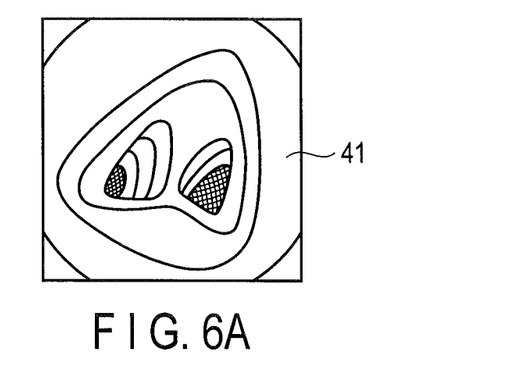
FIG. 6A is a diagram showing an example illustrating the weighting of pixels in a light receiving surface of an image pickup device.
Figure 6B:
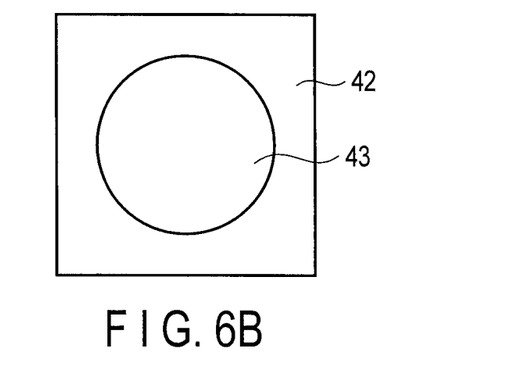
FIG. 6B is a diagram showing an example illustrating the weighting of the pixels in the light receiving surface of the image pickup device.

The inside of the lumen is mainly observed, so that an observer mainly watches the peripheral part of the display screen (visual field mask). For example, as shown in FIG. 6A, in the case of a bronchus, the observation target is the peripheral part of the display screen. In the case of such an organ, the pixels on the peripheral side of the imaging surface rather than the pixels on the central side are weighted, as shown in FIG. 6B. Whether the observation window 21 has fogged up is detected on the basis of the luminance level (contrast value) of an image signal acquired from the pixels for imaging color parts on the wall surface of the lumen.

[Selection 2] Flexible Scope (Stomach, Kidney, Bladder) Field

In the case of the stomach, the distal end may be bent to take an extensive view of the inside of the cavity. A visual field to be obtained can be caught on the central side of the display screen, and it is therefore desirable that the central side of the observation window 21 hot fog up. Thus, the pixels on the central side of the imaging surface rather than the pixels on the peripheral side are weighted. That is, the weighting is reverse to that in [Selection 1].

[Selection 3] Flexible Scope (Large Intestine)

The large intestine is in the lumen, but is a winding organ. Both the peripheral side and the central side of the display screen need to be observed, and it is desirable that the whole visual field not fog up. Thus, it is desirable that the whole surface of the observation window 21 not fog up, so that the pixels on the imaging surface are not independently weighted.

[Selection 4] Chest Surgery (Lung, Esophagus) Field

In the case of an operation on the lung or the esophagus (chest cavity), the cavity is deep, and there are many instances where the visual field is deep. The depth is great, and the operative field is therefore captured on the entire screen, so it is desirable that the entire surface of the observation window 21 not fog up at all. Thus, the pixels on the imaging surface are not independently weighted.

[Selection 5] Digestive Organ Surgery (Stomach, Large Intestine) Field

In the case of an operation on the stomach or the large intestine (abdominal cavity), the depth is not as great as that in the chest cavity, and the observation target (operative field and location) to be observed by the observer can be caught on the central side of the display screen. Therefore, it is desirable that the central side of the observation window 21 not fog up, and the pixels on the central side of the imaging surface rather than the pixels on the peripheral side are weighted. The weighting similar to the above-mentioned weighting in [Selection 2] is performed.

[Selection 6] Arthroscopic Field

In the case of arthroscopy, the cavity is extremely narrow, and the operative field therefore needs to be caught on the entire screen, so that it is desirable that the entire surface of the observation window 21 not fog up at all. Thus, the pixels on the imaging surface are not independently weighted.

[Selection 7] Endoscopic Paranasal Sinus Operation Field

In the case of an endoscopic paranasal sinus operation, the cavity is narrow but long, and the whole operative field is therefore caught on the entire screen, so that it is desirable that the entire surface of the observation window 21 not fog up at all. Thus, the pixels on the imaging surface are not independently weighted.

As described above, according to the present embodiment, when the observation window at the distal end of the endoscope has fogged up due to a temperature difference and humidity, the entire color of a taken observation picture becomes lighter, and the level of the luminance becomes lower, or a peak is generated in the luminance of a part of the entire display screen so that the distribution of the luminance level becomes narrower and the contrast becomes lower. This characteristic is used to compare the distribution or threshold of the luminance level of a taken observation image with the determination standard comprising a predetermined distribution of the luminance level or a predetermined threshold (FIG. 5) when the contrast of the photographic image has decreased. If the observation image is lower than the determination standard as a result of the comparison, it is determined that the observation window 21 has fogged up, and electric power is supplied to the fog prevention heater 22 so that the temperature of the observation window 21 is raised.

Therefore, according to the present embodiment, even if a temperature sensor that has heretofore been disposed in the distal end of the endoscope is not provided, the distribution (contrast) of the luminance level of the photographic image can be used to determine whether the observation window has fogged up, and the fog can be removed by raising the temperature of the heater. The configuration without the temperature sensor enables reducing the diameter of the distal end of the insertion portion and reduces the number of components, and is therefore advantageous in manufacturing costs.

Next, a modification of the first embodiment is described. The present modification provides a configuration equivalent to that of the endoscopic system shown in FIG. 1 and FIG. 2 according to the first embodiment described above, and is different in temperature control. The same components are described below with the same reference signs. In the first embodiment described above, the fog that is formed on the observation window when the insertion portion is inserted in the lumen is removed.

The present modification describes the operation of preventing the fog on the observation window 21 before the insertion portion 4 is inserted into the lumen, and in the situation in which the insertion portion 4 is taken out of the lumen during the observation and again inserted into the lumen.

First, when the temperature difference between the outdoor air temperature and the temperature inside the lumen is great under the usage environment, the temperature of the distal end 6 of the insertion portion 4 is closer to the outdoor air temperature. Thus, the difference between the temperature of the observation window at the distal end and the temperature inside the lumen is also great. Thus, if the insertion portion is inserted into the lumen as it is, the probability that the observation window fogs up is higher.

Thus, under an external environment before the start of insertion, the imaging unit 27 captures images of a space having no light-emitting objects without facing any article. When the space is simply captured, a taken observation image is darker than normal and is lower in luminance level, that is, lower in contrast because reflected light from the article which is illuminated by illumination light does not enter the image capture device 25. As described above, the determination circuit 36 compares the luminance level of the observation image with the determination standard, and determines that the observation window 21 has fogged up because the contrast is low. In accordance with this determination, the electric power supply circuit 38 supplies electric power to the fog prevention heater 22 from the heater power supply 37, and raises the temperature of the observation window 21. As a result, the temperature of the observation window 21 increases, and the temperature difference between the observation window 21 and the temperature inside the lumen is reduced.

Therefore, it is difficult for the observation window 21 to fog up when the distal end 6 is inserted into the lumen.

The same also applies to the situation in which the insertion portion 4 is taken out of the lumen during the observation and again inserted into the lumen. That is, if the insertion portion 4 is taken out of the lumen during the observation, the temperature of the observation window 21 at the distal end 6 also decreases closer to the outdoor air temperature, and the temperature difference between the observation window 21 and the temperature inside the lumen increases. If the imaging continues when the insertion portion 4 is taken out, an image of the space is captured, and an observation image low in luminance level, that is, low in contrast is taken because the space is captured, as described above. Therefore, it is determined that the observation window 21 has fogged up, and the electric power supply circuit 38 supplies electric power to the fog prevention heater 22, and raises the temperature of the observation window 21.

As described above, according to the present modification, an imaging operation is performed at the start of observation and before insertion, so that the temperature of the observation window 21 can be raised, and the temperature difference between the temperature of the observation window 21 and the temperature inside the lumen is eliminated before insertion, whereby the fog on the observation window 21 can be prevented. Similarly, if the imaging operation is continued when the distal end 6 is taken out of the lumen during the observation, the temperature of the observation window 21 can be raised, and the increase of the difference between the temperature of the observation window 21 and the temperature inside the lumen can be prevented. As a result of the prevention of the increase of the temperature difference, it is possible to prevent the fog on the observation window when the distal end 6 of the insertion portion 4 is again inserted into the lumen.

According to the present invention, it is possible to provide an endoscopic system in which a temperature sensor is not installed in the distal end of an insertion portion and which detects the state of fogging from a taken image and controls temperature raising of a heater.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. An endoscopic system with fog prevention for an observation window, the endoscopic system comprising:
   an endoscope in which the observation window is disposed at a distal end and which has an insertion portion to be inserted into a lumen;

an imaging sensor having an imaging surface comprising pixels to convert, into an image signal, an observation image which is focused through the observation window;

a fog prevention heater disposed in the vicinity of the observation window; and a processor comprising hardware, the processor configured to:

detect a distribution of a luminance level resulting from the image signal output by the pixels of the imaging sensor;

compare the distribution of the luminance level with a preset first determination standard and further compares the distribution of the luminance level with a threshold that is a preset second determination standard, and makes a determination so that the fog prevention heater performs a temperature raising operation on the basis of the comparisons; and control the fog prevention heater to raise the temperature of the observation window in accordance with the determination result in the determination section, wherein the first determination standard comprises a range of a distribution centering at a peak value of the distribution of the luminance level.

2. The endoscopic system according to claim 1, wherein the processor is further configured to set, as a determination standard, the distribution of the luminance level detected from the pixels weighted at a position on the imaging surface in accordance with a desired observation target that is to be observed.

3. An endoscopic system with fog prevention for an observation window, the endoscopic system comprising:

an endoscope in which the observation window is disposed at a distal end and which has an insertion portion to be inserted into a lumen;

an imaging sensor having an imaging surface comprising pixels to convert, into an image signal, an observation image which is focused through the observation window;

a fog prevention heater disposed in the vicinity of the observation window; and a processor comprising hardware, the processor configured to:

detect a distribution of a luminance level resulting from the image signal output by the pixels of the imaging sensor;

compare the distribution of the luminance level with a preset determination standard and make a determination so that the fog prevention heater performs a temperature raising operation when the distribution of the luminance level is less than or equal to the determination standard;

control the fog prevention heater to raise the temperature of the observation window in accordance with the determination result in the determination section; and when one of an entire display screen, a center of the display screen, and a peripheral side of the display screen is selected in accordance with an observation target that is desired to be observed, weight pixels on a central side of the imaging surface or pixels on a peripheral side of the imaging surface upon selection of the center of the display screen or the peripheral side of the display screen, and set, as a determination standard, the distribution of the luminance level detected from the weighted pixels.

4. The endoscopic system according to claim 3, wherein the weighting at the position on the imaging surface upon selection in accordance with the observation target comprises, a. weighting the pixels on the central side of the imaging surface if the center of the display screen in the observation target is selected, b. weighting the pixels on the peripheral side of the imaging surface if the peripheral side of the display screen in the observation target is selected, and c. not weighting the pixels on the imaging surface if the entire display screen in the observation target is selected.

* * * * *